(12) United States Patent
Whitlock

(10) Patent No.: US 6,912,872 B2
(45) Date of Patent: Jul. 5, 2005

(54) METHOD AND APPARATUS FOR PRODUCING A PURIFIED LIQUID

(75) Inventor: Walter H. Whitlock, Chapel Hill, NC (US)

(73) Assignee: The BOC Group, Inc., Murray Hill, NJ (US)

( * ) Notice: Subject to any disclaimer, the term of this patent is extended or adjusted under 35 U.S.C. 154(b) by 48 days.

(21) Appl. No.: 10/226,846

(22) Filed: Aug. 23, 2002

(65) Prior Publication Data
US 2004/0035148 A1 Feb. 26, 2004

(51) Int. Cl.[7] ................................................. F25J 3/00
(52) U.S. Cl. .......................................... 62/617; 62/905
(58) Field of Search ........................... 62/617, 620, 624, 62/636

(56) References Cited

U.S. PATENT DOCUMENTS

| | | | | |
|---|---|---|---|---|
| 4,152,130 A | * | 5/1979 | Theobald | 62/646 |
| 4,805,412 A | * | 2/1989 | Colley et al. | 62/648 |
| 4,932,147 A | | 6/1990 | David | |
| 5,711,167 A | * | 1/1998 | Ha et al. | 62/652 |
| 5,735,141 A | * | 4/1998 | Whitlock | 62/620 |
| 5,918,481 A | | 7/1999 | Pham et al. | 62/631 |
| 6,065,306 A | | 5/2000 | Ji et al. | 62/624 |
| 6,221,830 B1 | | 4/2001 | Miller et al. | 510/412 |
| 6,274,779 B1 | | 8/2001 | Merkel et al. | 570/134 |
| 6,327,872 B1 | | 12/2001 | Boyd et al. | 62/636 |
| 6,370,911 B1 | | 4/2002 | Zhou et al. | 62/626 |
| 6,387,161 B1 | | 5/2002 | Zhou et al. | 95/119 |
| 6,475,349 B1 | * | 11/2002 | McKeigue et al. | 159/43.1 |
| 2001/0004838 A1 | | 6/2001 | Wong et al. | |

FOREIGN PATENT DOCUMENTS

| | | |
|---|---|---|
| EP | 0 538 857 A1 | 4/1993 |
| EP | 0 805 324 A2 | 11/1997 |
| EP | 1 308 681 A1 | 5/2003 |
| EP | 1 342 968 | 9/2003 |
| FR | 1427522 | 3/1965 |

OTHER PUBLICATIONS

European Search Report; Munich; Aug. 26, 2004; Examiner Rico C. Martinez.
Abstract; EP 0 03255107.9.

* cited by examiner

Primary Examiner—William C. Doerrler
(74) Attorney, Agent, or Firm—David A. Hey

(57) ABSTRACT

The present invention provides generally a method and apparatus for purifying a liquid. More particularly, purification of a bulk liquid is performed by introducing a liquid stream to a purification vessel, which comprises both a distillation chamber for forming a purified vapor and an annular chamber for collecting a purified liquid that is condensed from the purified vapor. A refrigerant system provides thermodynamic efficiency in the purification method by directing waste heat generated in one part of the refrigerant system for heating duty in another part of the refrigerant system. The method and apparatus can be applied to producing purified carbon dioxide, nitrous oxide, ammonia and fluorocarbons.

30 Claims, 6 Drawing Sheets

METHOD AND APPARATUS FOR PRODUCING A PURIFIED LIQUID

FIELD OF THE INVENTION

The present invention relates to a method and apparatus for producing a purified liquid stream. More particularly, the present invention relates to a thermodynamically efficient purified liquid production method and apparatus using an improved purification chamber.

BACKGROUND OF THE INVENTION

Highly pressurized, purified liquid carbon dioxide is required for a variety of industrial processes. Often carbon dioxide as a bulk source stream is provided for purification as a vapor from a bulk carbon dioxide storage tank. For example, U.S. Pat. No. 6,327,872 discloses a method and apparatus for producing a pressurized high purity liquid carbon dioxide stream in which a carbon dioxide vapor feed stream is purified within a purifying filter and then condensed within a condenser. The resulting liquid is then alternately introduced and dispensed from two pressure accumulation chambers, which are heated by electrical heaters to pressurize the liquid to the desired delivery pressure.

However, system and size constraints often make it inefficient or impractical from a cost or logistical standpoint to manufacture purified liquid carbon dioxide from a vapor source. Indeed, carbon dioxide purification facilities using carbon dioxide from a bulk tank as a vapor source exhibit various complications, which become more problematic for high throughput systems. When a carbon dioxide vapor stream is used, there is a substantial heating load on the bulk tank pressure building system, which increases the likelihood of ice accumulating and blocking the pressure building system heat exchanger. In addition, such systems require the application of supplemental heating sources to maintain system pressure and vaporization. Such bulk tank vapor source systems also suffer from impurity buildup that results in significant time off-line for costly periodic maintenance and repair.

Therefore, a need exists for alternative method and apparatus for producing purified liquid carbon dioxide, or more generally a purified liquid, with improved performance, increased energy efficiency and reduced equipment cost.

SUMMARY OF THE INVENTION

The present invention generally relates to a method and apparatus for producing a purified liquid. The method and apparatus can be applied to the production of purified liquid carbon dioxide, nitrous oxide, ammonia and fluorocarbons.

One aspect of the present invention provides a method for producing a purified liquid stream. In one embodiment, a method comprises providing a feed stream source, introducing under pressure a feed stream from the source to a purification vessel, and supplying heat to the feed stream by heat exchange with a compressed refrigerant vapor stream in a first heat exchanger. The feed stream is distilled to form a purified vapor, which is condensed to form purified liquid by heat exchange with a refrigerant liquid stream in a second heat exchanger. The purified liquid stream is then withdrawn from the purification vessel. The refrigerant liquid stream and the compressed refrigerant vapor stream are provided in a refrigerant flow network comprising the first and second heat exchangers.

In another embodiment, the method comprises providing a liquid material source and introducing under pressure a liquid feed stream from the liquid material source to a purification vessel via a substantially free flow connection, with the purification vessel comprising a distillation column assembly and a collection chamber positioned annularly about the distillation column assembly. The liquid feed stream is purified in the distillation column assembly to produce a purified liquid, which is stored in the collection chamber.

Another embodiment relates to a method comprising providing a liquid material source and introducing, under pressure, a liquid feed stream from the source to a purification vessel via a substantially free flow connection. The liquid material is selected from the group consisting of carbon dioxide, nitrous oxide, ammonia and fluorocarbons. The purification vessel comprises a distillation column assembly and a collection chamber positioned annularly about the distillation column assembly. The liquid feed stream is vaporized into a vapor; which is directed through a distillation column in the distillation column assembly to purify the vapor. The purified vapor is condensed into a purified liquid; which is collected in the collection chamber to a predetermined volume. When the predetermined volume has been exceeded, a portion of the purified liquid is returned from the bottom of the collection chamber to the distillation column assembly.

In yet another embodiment, the method comprises providing a liquid material source and introducing, under pressure, a liquid feed stream from the source to a purification vessel via a substantially free flow connection. The liquid material is selected from the group consisting of carbon dioxide, nitrous oxide, ammonia and fluorocarbons. The purification vessel comprises a distillation column assembly and a collection chamber positioned annularly about the distillation column assembly. The liquid feed stream is vaporized to produce a vapor; which is directed through a distillation column of the distillation column assembly to produce a purified vapor. The method further comprises providing a condenser refrigeration system comprising at least one condenser inside the distillation column assembly; condensing the purified vapor into a purified liquid in the at least one condenser; and collecting the purified liquid in the collection chamber to a predetermined volume. An amount of the purified liquid is withdrawn from the collection chamber and subjected to a pressure of from about 1100 to about 3000 psia. Heat byproduct from the condenser refrigeration system is directed to a heat exchanger for heating the purified liquid to a predetermined delivery or storage temperature; and the heat byproduct is generated in part by the condensation of the purified vapor in the at least one condenser.

Another aspect of the invention relates to an apparatus for producing a purified liquid stream. In one embodiment, the apparatus comprises a purification vessel in connection with a bulk material source. The purification vessel comprises an intake for admitting a bulk material feed stream from the source, a distillation assembly comprising a distillation column for forming a purified vapor from the bulk material feed stream and a condenser for condensing the purified vapor into a purified liquid, and an annular collection chamber surrounding the distillation column for collecting the purified liquid. The apparatus also comprises a refrigerant flow network in communication with the bulk material feed stream and the purified vapor for providing heat to the bulk feed stream and cooling to condense the purified vapor to the liquid after the purified vapor exits the distillation column. The apparatus can be used for producing purified carbon dioxide, nitrous oxide, ammonia and fluorocarbons.

Another aspect of the invention provides a purification vessel comprising: a distillation column assembly having an inlet for admitting an amount of material to be purified and an outlet for releasing an amount of purified material, a heat exchanger in contact with the material to be purified, a packed distillation column having a column inlet and column outlet through which material to be purified passes, the exchanger positioned below the column inlet, and a condenser located proximate to the column outlet; and an annular chamber surrounding the packed distillation column, the annular chamber having an inlet for collecting purified material and an outlet for releasing the collected purified material.

Yet another aspect of the invention provides an annular chamber for collecting purified liquid carbon dioxide from a distillation column comprising a substantially cylindrical vertical inner wall, a chamber bottom extending radially outward from the inner wall a predetermined distance to a substantially cylindrical vertical outer wall, the inner wall having a diameter dimensioned to surround a packed distillation column.

BRIEF DESCRIPTION OF THE DRAWINGS

While the specification concludes with claims distinctly pointing out the subject matter that applicants regard as their invention, it is believed that the invention will be better understood when taken in connection with the following drawings.

DETAILED DESCRIPTION OF THE INVENTION

Figure 1:
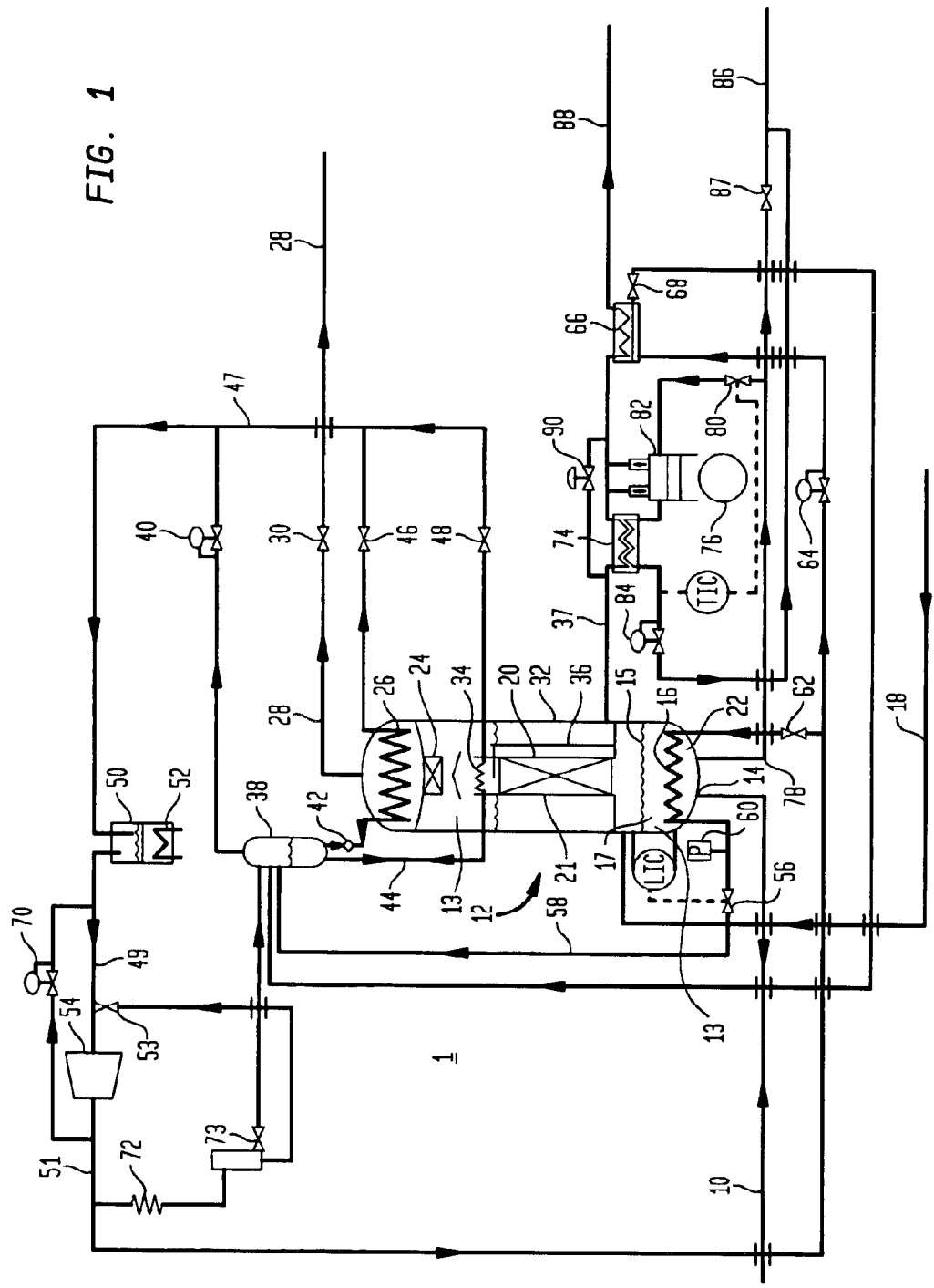
FIG. 1 is a schematic representation of one embodiment of the process and apparatus of the present invention.

With reference to FIG. 1, an apparatus 1 is illustrated in accordance with the present invention. A feed stream of liquid carbon dioxide, such as from a standard 300 psig bulk tank (not shown in FIG. 1) enters the apparatus 1 via line 10. Line 10 connects to the bottom of purification and storage vessel 12 at port 14. Purification and storage vessel 12 comprises a distillation column assembly 13 surrounded by an annular collection chamber 32 that is preferably an integral chamber—i.e., as an integral component of the purification vessel 12. Line 10 is specifically designed to allow the substantially free flow (without significant restriction) of carbon dioxide back and forth from the bulk carbon dioxide supply to the distillation column assembly 13 of purification and storage vessel 12. According to the present invention, it may be desirable to slow down the free flow rate of liquid carbon dioxide into the system 1 to ensure that the level control system has adequate time to respond to the influx of material. Since at least some degree of check on a pure free flow system may be in effect at some times during system operation, there is more precisely a substantially free flow arrangement between the bulk carbon dioxide source and the system 1. During operation, carbon dioxide enters the bottom of the purification and storage vessel 12 into distillation column assembly 13 and begins to fill the distillation column assembly 13 at least to a level 15 that substantially submerges the boilup heat exchanger 16.

The level of liquid carbon dioxide admitted to the purification and storage vessel 12 is controlled by adjusting the duty in the heat exchanger 16 to maintain a level setpoint as the liquid carbon dioxide 17 during operation is vaporized continuously from a liquid state. When the liquid carbon dioxide level is below setpoint, less duty is supplied resulting in a reduced carbon dioxide vaporization rate. When the liquid carbon dioxide level is above setpoint, more duty is supplied causing an increased carbon dioxide vaporization rate. It is understood that the distillation column assembly 13 has three regions: a boilup region in the bottom where liquid carbon dioxide is exposed to heat for the purpose of vaporizing the liquid; a distillation region located above the boilup region comprising a distillation column; and a condensing region above the column whereby the purified vapor emerging from the column is exposed to a heat exchanger for purposes of condensing the purified vapor into purified liquid carbon dioxide. The distillation column can generally be either a packed column or any suitable trayed column, although a packed column is used in this discussion for illustrative purpose.

In one embodiment of the present invention, waste carbon dioxide vapor from an online application is redirected via a carbon dioxide vapor recycle line 18 to the carbon dioxide purification and storage vessel 12 from, for example, an abatement and recovery process. (Not shown in FIG. 1—See 121 in FIG. 2). The recycle line 18 as shown enters the purification and storage vessel 12 at a point above the level of the liquid carbon dioxide and the recycled carbon dioxide vapor combines or commingles with the bulk carbon dioxide delivered to the vessel via line 10.

As heat exchanger 16 causes the vaporization of the liquid carbon dioxide 17, carbon dioxide vapor flows upwardly though a first packed distillation column 20 and contacts condensed liquid carbon dioxide moving downwardly through column 20. Such counter-current liquid-vapor contact removes heavy impurities from the ascending carbon dioxide vapor and returns the impurities to the liquid carbon dioxide 17 in the bottom 22 of vessel 12. Some carbon dioxide vapor emerges from the top of the first column 20 and is substantially free of heavy impurities. Carbon dioxide liquid 17 located at the bottom 22 of vessel 12 is periodically vented via line 78 to prevent an excessive buildup of impurities in the vessel 12.

As shown in FIG. 1, the majority of the ascending carbon dioxide vapor emerging from the top of the first column 20 flows into the bottom of the second packed distillation column 24. Once in the second column 24, the ascending carbon dioxide vapor contacts condensed carbon dioxide liquid descending through the second column 24. This counter-current liquid-vapor contact concentrates light impurities in the ascending carbon dioxide vapor and decreases the concentration of the light impurities in the descending liquid carbon dioxide. The carbon dioxide vapor emerging from the top of the second packed column 24 is partially condensed by heat exchanger 26 resulting in condensed carbon dioxide being returned to the top of second packed column 24 as reflux. The flow rate of the reflux is controlled by setting the duty in the heat exchanger 26. Line 28 extends from the top of the second packed column 24 within distillation chamber assembly 13 and contains valve 30, which is periodically opened to vent accumulated vapor containing light or non-condensable impurities.

The liquid reflux entering the top of the second packed column 24 passes down through the column and is collected into the annular collection chamber 32 that surrounds the first packed column 20 in distillation chamber assembly 13. The flow rate of the liquid product collection is controlled by setting the duty in heat exchanger 26. Heat exchanger 34 is used to generate liquid reflux for the first packed column 20. The liquid reflux thus flows down the first packed column 20 to the bottom of distillation chamber 13 and is ready once again for boilup. Heat exchanger 34 provides reflux only for the first packed column 20.

As described above, liquid carbon dioxide condensed by heat exchanger 26 is collected as product in the annular collection chamber 32 that surrounds the first packed column. The annular collection tank 32 is provided with an overflow tube 36 that returns liquid carbon dioxide from the bottom of the annular tank to the top of the first packed column 20 where it serves as an additional liquid reflux. The overflow tube 36 ensures that carbon dioxide inventory is held on a first in, first out basis. In other words, according to one embodiment of the present invention, the oldest carbon dioxide at the bottom of the annular collection chamber 32 is returned to the first packed column 20, and the annular tank 32 is continuously purged by incoming purified carbon dioxide during periods of low carbon dioxide product demand. Alternatively, liquid carbon dioxide condensed by heat exchanger 26 could be directed to the bottom of the annular collection chamber 32 and the collection chamber 32 could be provided with an overflow that returns liquid carbon dioxide from the top of the annular chamber 32 to the top of the packed distillation column 20. This would also return older carbon dioxide, now at the top of the annular chamber 32 to the packed column 20. Purified liquid carbon dioxide product is withdrawn from the bottom of the annular collection chamber 32 as needed by the pressurization and delivery system of the apparatus.

During periods of low product demand, as pressure within the vessel 12 builds up, it is understood and indeed is one advantageous aspect of the present invention that back pressure in the system may allow a flow of impure liquid carbon dioxide from the bottom of vessel 12 to flow through the free flow line 10 back into the bulk liquid carbon dioxide source due to the substantially free flow nature of line 10. For example, when, as a temporary condition, more carbon dioxide is received from the recycle vapor line 18 than is withdrawn from the annular collection chamber 32 as product, the excess carbon dioxide is condensed to liquid and sent to the bulk liquid carbon dioxide source via the free flow line 10 for storage. When the temporary condition of excess recycle vapor is over, the condensed liquid placed in the bulk liquid source is withdrawn and processed normally as previously described. One resulting advantage from this efficient use of recycle vapor returned to the purification vessel is to reduce consumption of the bulk source liquid carbon dioxide in the purification system.

All duty for both cooling and heating is provided by a single closed cycle refrigeration system. The refrigerant selected for reference purposes is preferably R22 but may be any suitable refrigerant such as, but not limited to R134 A depending upon commercial objectives. Substitution of refrigerant may result in different system pressures and temperatures as appropriate. The refrigerant accumulator 38 is sized to contain the entire inventory of refrigerant as liquid. The accumulator 38 separates liquid refrigerant from the mixed phase feed streams and ensures that saturated liquid refrigerant is available as feed to the condenser heat exchangers 26, 34. Pressure is controlled by venting refrigerant vapor through valve 40 to the refrigerant compressor 54. The two condenser heat exchangers 26, 34 both take liquid refrigerant from the refrigerant accumulator 38 through a free flowing connection line 42, 44 respectively. Liquid refrigerant is intended to flow freely through lines 42, 44 without restriction. Liquid refrigerant enters the bottom of each condenser 26, 34, is vaporized and exits the top of the heat exchangers as a vapor. The duty is controlled by controlling the flow rate of vapor refrigerant leaving the top of each heat exchanger. The level of liquid refrigerant inside each heat exchanger is self-adjusting so long as the maximum heat exchange capacity is not exceeded.

Flow control valves 46, 48 are used to control the vapor flow rate and therefore the duty of heat exchangers 26, 34 respectively. After leaving the valves, the refrigerant vapor flows on to the refrigerant compressor suction manifold 47.

A liquid trap 50 in the suction manifold collects any liquid refrigerant that may be present and prevents it from entering the compressor where it could cause damage. The collected liquid is slowly vaporized either by electric heaters 52 or other means as appropriate. Refrigerant vapor from the suction manifold is compressed by a compressor 54 and discharged as a hot high pressure gas. A first portion of the compressor discharge refrigerant vapor is sent to boilup heat exchanger 16 where it condenses to liquid causing boilup of the liquid carbon dioxide in the bottom of distillation chamber 13. High pressure liquid refrigerant accumulates inside heat exchanger 16 and the duty is controlled by controlling the flow rate of liquid refrigerant leaving the heat exchanger 16 by flow control valve 56. When more duty is required to reduce the carbon dioxide level within the annular collection chamber 32, valve 56 is opened further allowing more liquid refrigerant to leave heat exchanger 16 and consequently more vapor refrigerant to enter and condense and supply additional duty. When less duty is required, valve 56 is closed, further causing a reduction in the flow rate of refrigerant vapor and a consequent decrease in duty. The liquid refrigerant passing through valve 56 is sent to the refrigerant accumulator 38 via line 58.

As an alternative, duty in heat exchanger 16 can be controlled by using valve 56 and pressure transducer 60 as a back pressure control and valve 62 to control refrigerant flow rate. The back pressure setpoint is high enough that the dew point of R22 vapor inside heat exchanger 16 provides enough temperature differential to drive heat transfer against the boiling liquid carbon dioxide. For example, a pressure setpoint of 50 psia would give a R22 dew point of −11C and provide a temperature differential of 8.8C against boiling carbon dioxide at 280 psia and −19.8C. Duty in heat exchanger 16 is controlled by controlling flow rate of R22 vapor through valve 62 as required to maintain the liquid carbon dioxide level setpoint. This approach may allow the duty in heat exchanger 16 to be changed more quickly because the liquid R22 inventory within heat exchanger 16 can be removed or added more quickly.

A second portion of the compressor discharge refrigerant vapor is sent through pressure regulator 64 and then on to the product warming heat exchanger 66. The function of regulator 64 is to reduce the pressure so that the dew point of the resulting reduced pressure refrigerant vapor is close to the desired delivery temperature of the high pressure purified liquid carbon dioxide product. The reduced pressure refrigerant vapor is fed beneath a pool of liquid refrigerant in heat exchanger 66 to remove any superheat. The resulting de-superheated vapor condenses at the dew point established by regulator 64 and warms the high-pressure purified liquid carbon dioxide product to a temperature approximating the dew point. As shown in FIG. 1, the level of condensed liquid refrigerant is controlled by a float operated level control valve 68 and sent to the refrigerant accumulator 38.

When needed, a portion of the compressor discharge refrigerant vapor is returned to the compressor suction to prevent the suction pressure from falling below desired or required operating specifications. A hot gas bypass system consisting of pressure regulator 70 senses pressure in the compressor suction inlet 49 and opens to return refrigerant vapor from the compressor discharge 51 to maintain the compressor suction pressure within specifications.

The remaining balance of the compressor discharge refrigerant vapor is sent to an air-cooled condenser 72 where it is condensed. Refrigerant flow rate is controlled by a float-operated valve 73 and the liquid refrigerant is sent to the refrigerant accumulator 38.

To prevent the compressor suction from exceeding temperature specifications, a temperature control valve 53 opens to supply a controlled flow rate of liquid refrigerant from the condenser 72 to the compressor suction. The liquid refrigerant flashes to vapor and cools the compressor suction. Suction cooling is required only for extended periods of operation with hot-gas bypass flow rates.

Purified liquid carbon dioxide leaves the annular collection chamber 32 via line 37 and is first sub-cooled in heat exchanger 74 and then pumped to nominal pressure of from about 1100 to about 3000 psig pressure by pump 76. To ensure NPSH requirements of the pump 76 are met, both the incoming liquid carbon dioxide and the pump itself are cooled below the boiling point of the purified liquid carbon dioxide. The refrigeration to accomplish this cooling is provided by flashing liquid carbon dioxide taken from the bottom of vessel 12 in the distillation chamber 13 as shown via line 78. This liquid carbon dioxide contains an increased concentration of heavy impurities and must be vented from the system regularly. According to the present invention, however, at least part of the refrigeration energy is recovered from this waste stream by heat exchange with the pump 76 and liquid carbon dioxide from line 37. As shown in FIG. 1, after passing through flow control valve 80, the carbon dioxide acting as refrigerant passes through the pump jacket heat exchanger 82 and pump feed heat exchanger 74 where it is vaporized. The resulting vapor passes through back pressure regulator 84 which sets the flash pressure and then flows out the heavies vent 86 where it is discharged to the atmosphere. This efficient use of the waste stream cannot readily be achieved in other purification systems, e.g., one in which a vapor carbon dioxide feed stream is supplied from a bulk tank. In those systems, accumulation of heavy impurities in the liquid carbon dioxide supply will eventually require the entire liquid content to be discarded. Provision is also made to separately vent liquid via valve 87 from the bottom of vessel 12 if required for control of heavy impurity concentration in vessel 12.

The high pressure, but still cold purified liquid carbon dioxide which leaves pump 76 is warmed to ambient temperature in heat exchanger 66 to prevent possible condensation of atmospheric moisture on the lines carrying high pressure purified liquid carbon dioxide product out of the inventive system and apparatus 1 via line 88. A back pressure regulator 90 ensures that the carbon dioxide pump 76 is not damaged should the flow of high pressure carbon dioxide product become blocked.

It is understood that the purification and storage vessel will be made from materials able to withstand the processing regimens and requirements of the system which is understood to be a low temperature system. For example, the annular storage chamber and distillation column assembly are preferably made from 304, 316 and 316L stainless steel, with 304 stainless steel being most preferred. Furthermore, the apparatus and method disclosed above can also be used with other suitable liquids, such as nitrous oxide, ammonia and fluorocarbons.

Figure 2:
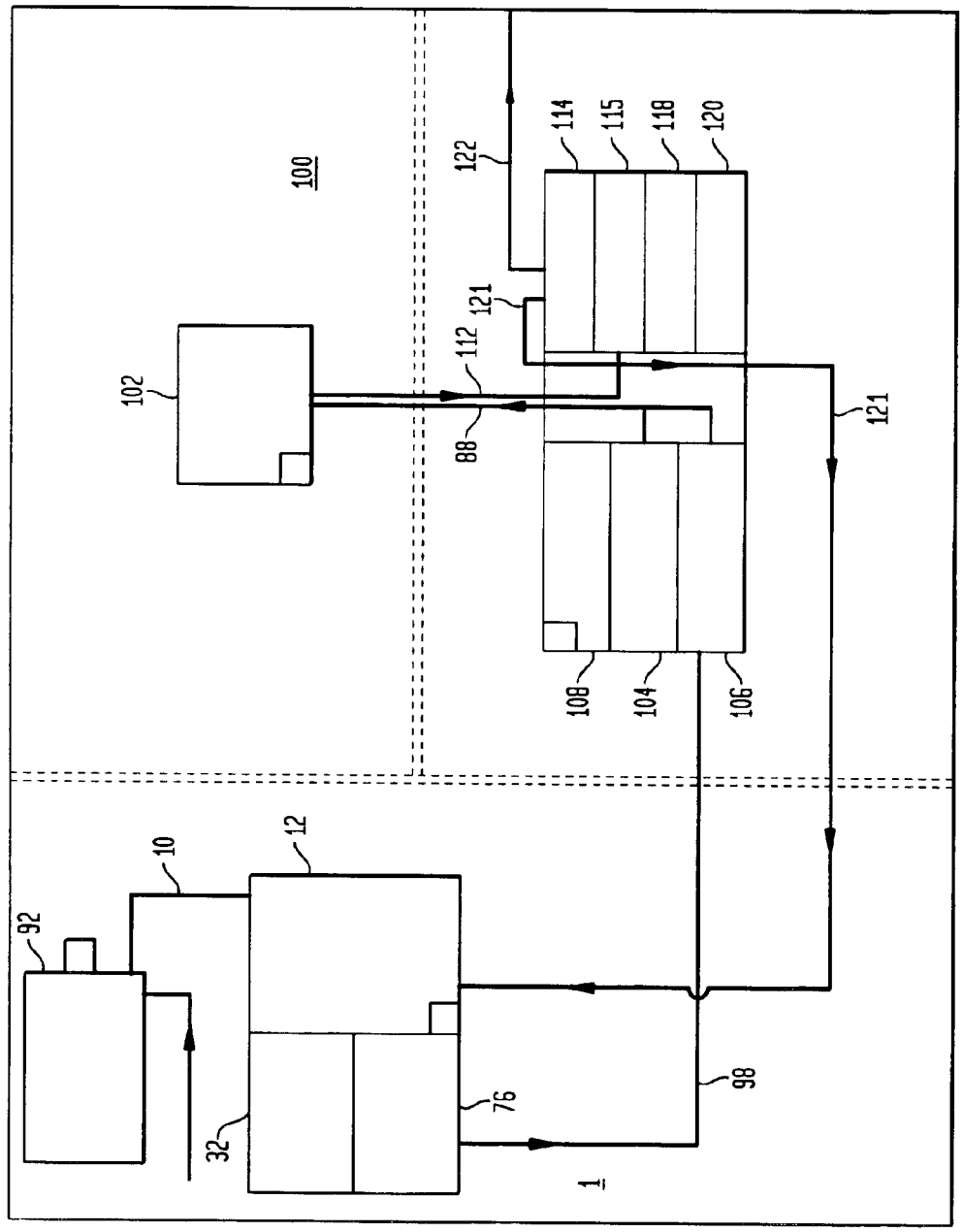
FIG. 2 is a schematic representation of one embodiment of the process and apparatus of the present invention implemented in an application.

FIG. 2 shows the carbon dioxide supply system 1 of FIG. 1 incorporated into a desired point of use application 100. In this illustration, high pressure carbon dioxide liquid from system 1 is delivered for use in a process tool 102. A waste stream containing carbon dioxide from the process tool is then treated and recycled back to system 1 for purification and re-use. Line 10 directs the bulk liquid carbon dioxide from a bulk carbon dioxide source 92 to the purification vessel 12. The purification vessel is in communication with a low pressure liquid accumulator 32 that is preferably an annular tank contained within the purification and storage vessel 12. A high pressure liquid pump 76 establishes and maintains a delivery of the pure carbon dioxide to equipment 106, e.g., at a pressure of at least about 1100 psig, preferably from about 1100 to about 3500 psig, and more preferably between about 3000 and about 3500 psig, and a temperature of about 20C to about 40C. Depending on the specific application, however, other delivery pressures may also be used.

In the illustrated embodiment, high pressure purified liquid carbon dioxide is directed via line 98 of system 1 to a pure carbon dioxide accumulator 106 (high pressure liquid). Depending on the application, the purified liquid carbon dioxide may also be directed to other equipment 104 and/or 108 (e.g., mixer for mixing carbon dioxide with other fluids, or temperature and pressure controller) prior to being supplied to the tool 102. Used carbon dioxide is vented from the tool environment 102 along with impurities via line 112 for processing through liquid/vapor separator 115 and various waste treatment stages, which may include, for example, vapor scrubbing 114, chemical abatement 118, and waste packaging and storage 120. Cleansed carbon dioxide vapor is then purged to the atmosphere via line 122 or directed via line 121 (low pressure vapor) to carbon dioxide vapor recycle line 18 of system 1.

As an example, the application 100 may be a processing step in semiconductor fabrication that requires the use of high pressure, or supercritical, purified carbon dioxide, e.g., wafer drying, resist stripping, etch residue removal, among others. In this case, tool 102 is any suitable processing tool such as a dryer, resist stripper or cleaner located inside a clean room (or the "fab" area), while support equipment 104, 106, 108 and waste treatment equipment 114, 115, 118 and 120 are typically located in the "sub-fab" area, with supply and return lines coupling these equipment to the carbon dioxide supply system 1 located outdoors. It is also understood that controllers and sensors are provided in many of the equipment in such an application in order to allow proper process monitoring, control and automation.

As stated above, in one embodiment of the present invention, establishing a substantially free flowing connection between the bulk carbon dioxide source and the purifying vessel allows the liquid carbon dioxide to move back and forth as needed between the bulk carbon dioxide storage tank source and the purifying vessel, which in the preferred embodiment of the present invention is a multi-purpose vessel. This ensures that the pressures are substantially equal between the source tank and the vessel. As carbon dioxide is removed from the vessel, such as to satisfy product demand, the pressure within the vessel decreases and liquid carbon dioxide flows from the bulk storage tank to re-fill the vessel. The purification vessel of the present invention as shown in FIGS. 1 and 3–6 comprise two packed columns within a first chamber to effect distillation and purification of the liquid carbon dioxide, along with an annular storage chamber positioned to surround the first distillation column.

Figure 3:
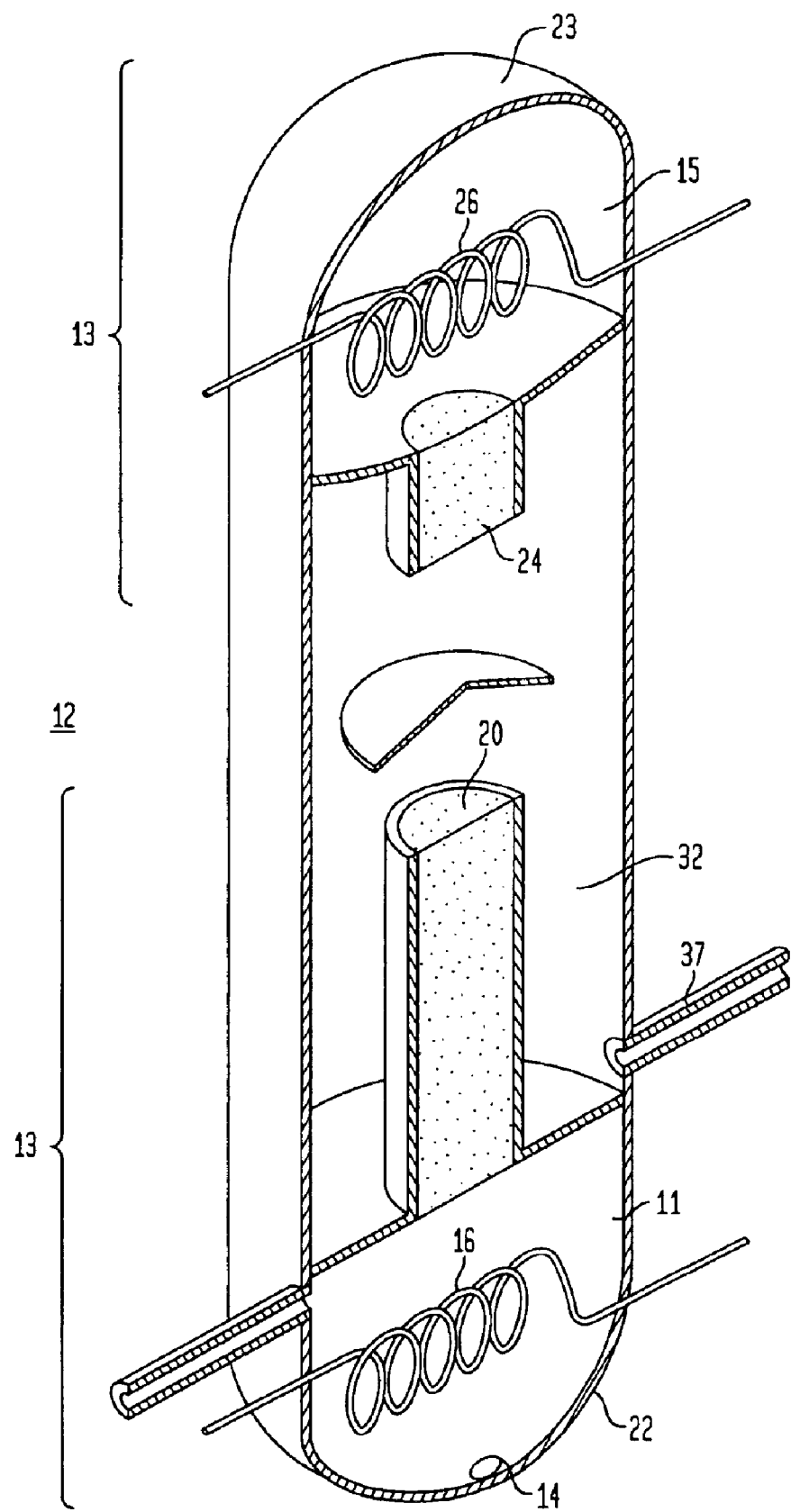
FIGS. 3–5 are exposed perspective views of embodiments of the purification vessel of the present invention.
Figure 4:
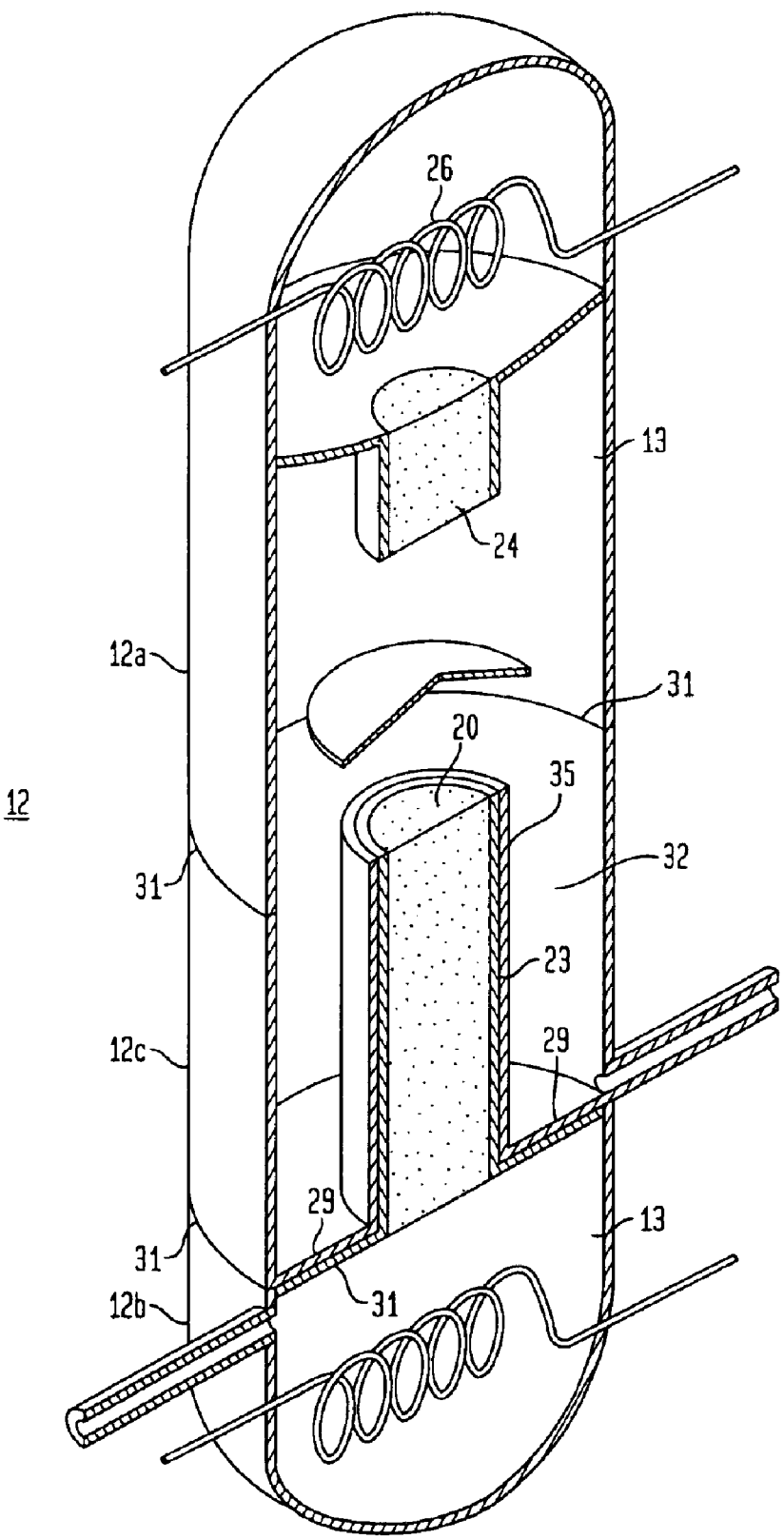
Figure 5:
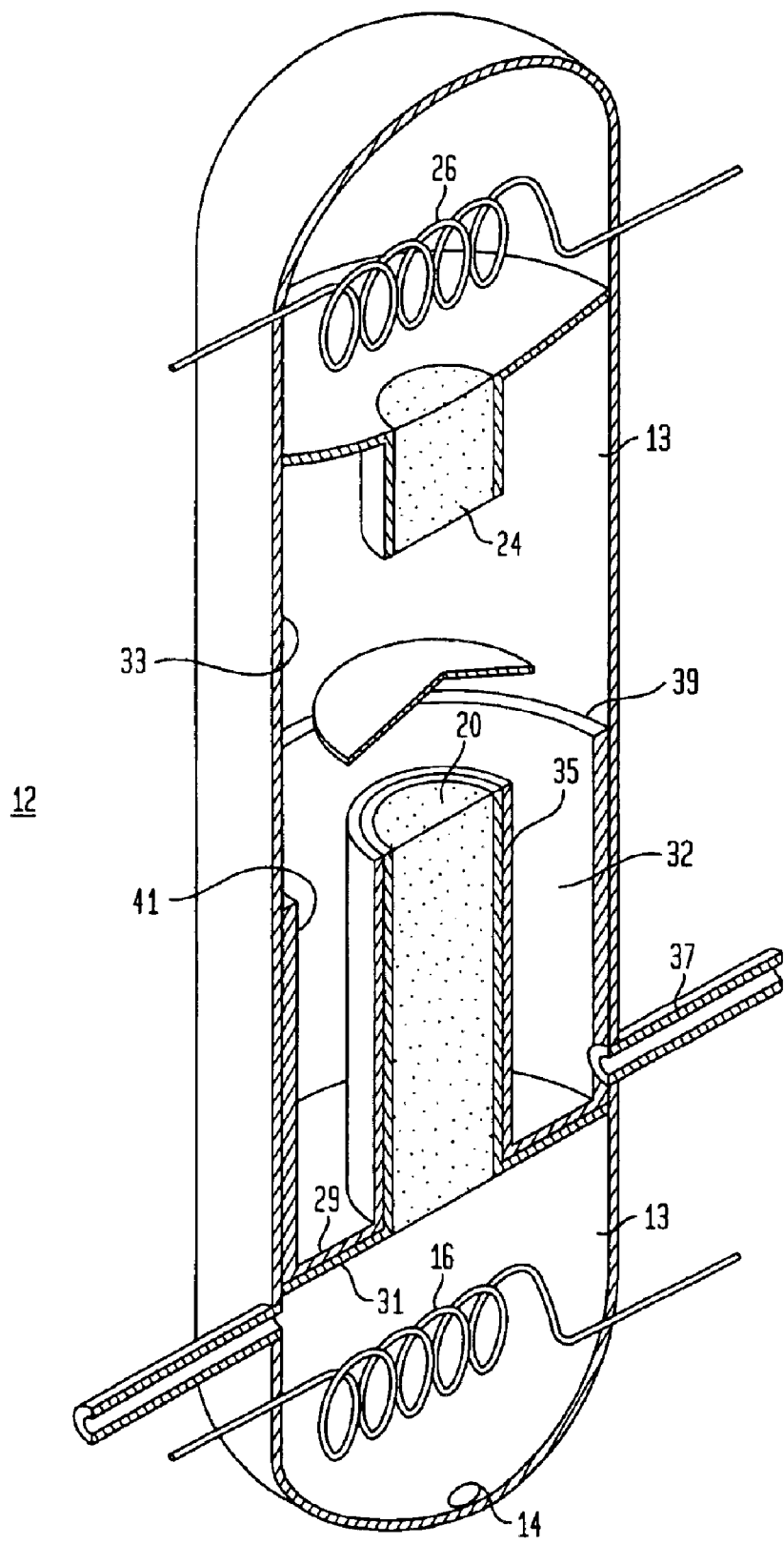

FIGS. 3–5 show an exposed perspective view of the purification system. In one embodiment of the present invention, as shown in FIG. 3, the purification vessel 12 comprises two major functions or systems—that of purification and storage of the purified liquid. Unlike most known carbon dioxide purification systems, which rely on the use of filter or a single condensation step, the present invention uses distillation for purification, and in particular, multistage distillation with at least one trayed or packed column. The distillation column assembly 13 comprises the area for boilup 11 at the bottom 22 of vessel 12, packed distillation columns 20, 24 and condensing area 15 located at the top 23 of the purification vessel 12. Purified carbon dioxide vapor condenses and descends within the purification vessel 12 and collects within a region of the purification vessel 12 forming the annular collection chamber 32. In this way, the purification vessel also stores the purified liquid carbon dioxide until it is ready to be directed from the annular chamber 32 via outlet 37 to the point-of use of other use demand. This contrasts with other purification systems, e.g., filter purifiers, where separate purification and storage vessels are required.

In a further embodiment, as shown in FIG. 4, the annular collection chamber 32 is shown as formed by a separate substantially cylindrical piece 12c that is welded via weld seals 31 to the upper 12a and lower 12b sections of the purification vessel. In this embodiment, the inner cylindrical wall 35 of the piece 12c has a diameter about equal to or just slightly larger than the diameter of the outer wall 23 of the distillation column 20. As shown, the floor 29 of piece 12c is proximate to flange 31 of bottom section 12b. Therefore, in this embodiment the annular storage chamber 32 is created by a separate structure 12c that is assembled with the other structural components to make up the overall purification vessel 12.

In a still further embodiment, FIG. 5 shows the annular collection chamber 32 as formed by a discrete annular storage vessel 39 dimensioned to fit within purification vessel 12. In this embodiment, the annular storage vessel 39 has a substantially cylindrical inner wall 35 with a diameter dimensioned to be equal to or slightly exceed the diameter of the outer wall of the distillation column 20. In addition, the diameter of the substantially cylindrical outer wall of the annular storage vessel 39 is slightly less than the diameter of the inner wall 33 of the purification vessel. Therefore in this embodiment, the annular storage chamber 32 is created by a separate structure 39 that acts as an inset piece onto the distillation column for the collection of the purified liquid carbon dioxide product.

Figure 6:
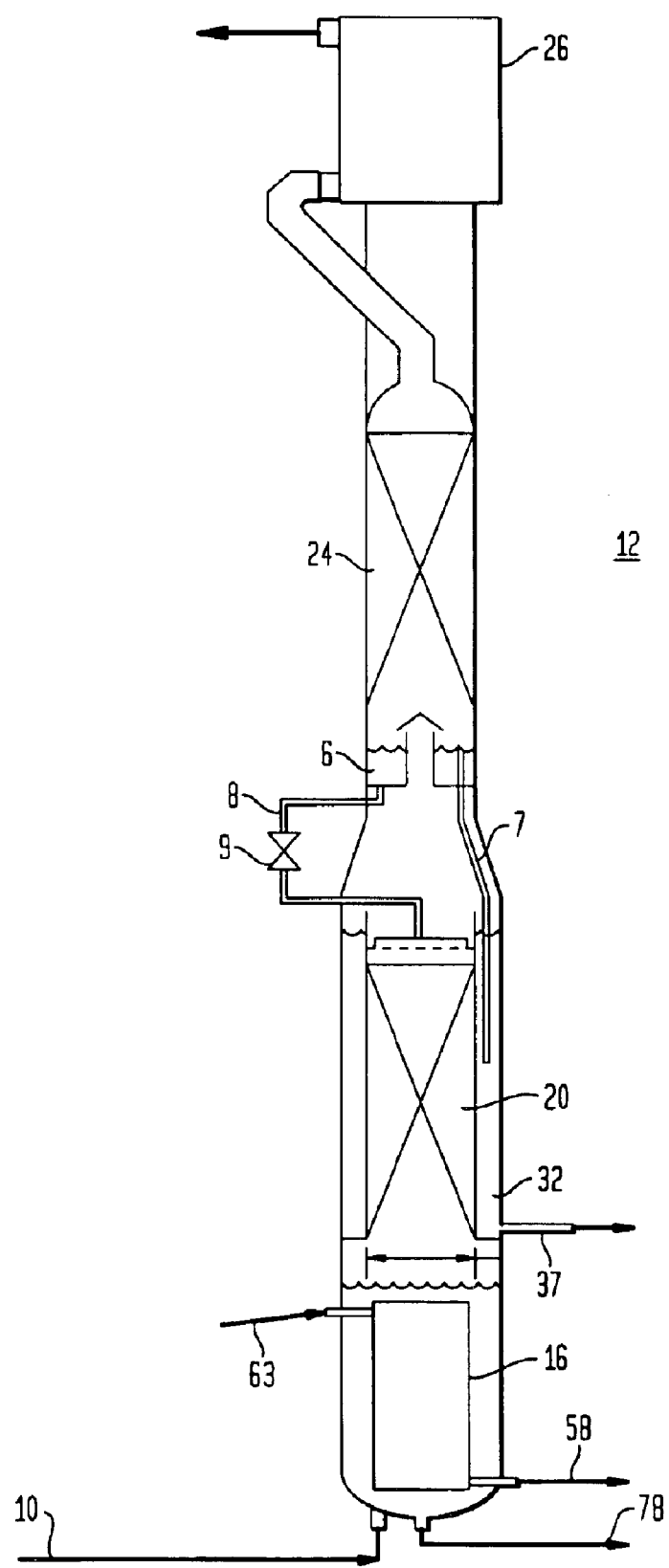
FIG. 6 is a schematic view of another embodiment of the purification vessel of the present invention.

FIG. 6 is a schematic representation of another purification vessel of the present invention. In this embodiment, the vessel 12 comprises a distillation column assembly that comprises a heat exchanger 16, first distillation column 20, second distillation column 24 and condenser 26. Annular collection chamber 32 is shown encasing the first distillation column 20. Carbon dioxide liquid from condenser 26 is provided as reflux to the top of distillation column 24. Purified liquid carbon dioxide collected at a reservoir 6 at the bottom of column 24 is directed to the annular chamber 32 via duct 7. In this embodiment, liquid carbon dioxide from reservoir 6 is also provided as reflux to distillation column 20 via duct 8 and control valve 9.

Embodiments of the present invention provide various features and advantages, some of which are highlighted below. For example, enhanced conservation of thermal energy is achieved by coupling the product condenser 26 and boil-up heat exchanger 16 to allow efficient use of thermal energy within the refrigerant flow network. Liquid carbon dioxide in the bottom of the vessel is vaporized in a boil-up heat exchanger 16 by heat transfer with a condensing refrigerant vapor. The refrigerant vapor, which is a portion of a compressed refrigerant vapor stream in a refrigerant flow network (used for refrigeration duty in other equipment or elsewhere in the process), enters heat exchanger 16 via inlet 63. In general, a large portion of the heat contained in the refrigerant vapor originates from the condensing duty at condenser 26. Heat transfer between the refrigerant vapor and the liquid carbon dioxide causes liquid carbon dioxide to vaporize and the refrigerant vapor to condense. The condensed refrigerant exits the heat exchanger 16 via line 58 and returns to the refrigerant flow network. This arrangement allows the otherwise wasted heat from the refrigerant vapor, also referred to as heat byproduct, to be used for vaporization of liquid carbon dioxide. By contrast, in known processes where vapor carbon dioxide is drawn from the bulk source and a refrigerant stream is used to condense the vapor carbon dioxide, all the heat resulting from the condensing refrigerant vapor is rejected as waste heat to the atmosphere. Additional energy must often be supplied, such as by additional heaters, to meet heating needs in other parts of the system or process, e.g., for vaporization of the carbon dioxide feed stream.

Still further, in the present invention, the flow rate of the condensing refrigerant is controlled by using a control valve (shown as valve 56 in line 58 of FIG. 1) to adjust the flow rate of liquid refrigerant leaving the boil-up heat exchanger 16 based on the level of liquid carbon dioxide in the bottom of the purification vessel 12. As shown in FIG. 1, the level of liquid carbon dioxide in the purification vessel 12 is monitored by a level indicating controller (LIC), which also provides a control signal to control valve 56. When the liquid level is above a predetermined volume or set point, the control valve 56 opens, further increasing the refrigerant flow rate through heat exchanger 16 and increasing the boil-up rate of the carbon dioxide causing the level to decrease. When the liquid level is below set point, the refrigerant flow rate is decreased causing the carbon dioxide level to increase. In addition, according to the present invention, the resulting liquid refrigerant is directed to a liquid refrigerant storage vessel to be used elsewhere in the purification process.

Furthermore, the liquid refrigerant is withdrawn from liquid refrigerant storage 38 to operate both the reflux and product condensers (or heat exchangers) 34 and 26. One preferred way to control both condensers is to regulate the flow rate of refrigerant vapor leaving each condenser using, for example, flow control valves 46 and 48, and allow free access (free flow) between the condenser and the liquid refrigerant storage vessel for liquid refrigerant to both enter and exit the condenser. With this free flow design, the level of refrigerant insider the condensers are self-adjusting, and improved control of the condenser duty can be achieved.

Yet another feature of the present apparatus—the overflow tube 36 in the collection chamber 32, also contributes to performance enhancement. When the annular collection chamber 32 (surrounding the distillation columns) becomes full, liquid carbon dioxide is removed via overflow tube 36 from the bottom of the chamber 32. Thus, freshly purified liquid carbon dioxide is used to displace the oldest carbon dioxide, which is transferred from the bottom of the annular collection chamber 32 to the top of the distillation column 20 where it is re-purified. When the system demand for product is less than capacity, the unneeded or extra capacity is used to re-purify the previously accumulated purified liquid carbon dioxide product. The increased liquid reflux to the distillation column 20 also results in a higher purity product. With this arrangement of the overflow tube 36, the refrigeration system continues to run as before during periods of low demand without requiring adjustment, and less liquid carbon dioxide is withdrawn from the bulk source carbon dioxide. By contrast, in the absence of the overflow tube 36, adjustment of the refrigeration system would be required in order to turn down the duty of the condenser 26.

While the present invention has been described with reference to preferred embodiments, as will occur to those skilled in the art, numerous additions, changes, and omissions can be made without departing from the spirit and scope of the present invention. For example, while two distillation columns are used in the above illustrations, embodiments of present invention can also be practiced in a system with a single distillation column. Furthermore, although it is advantageous to provide to the purification vessel a feed stream comprising primarily of liquid, certain aspects or embodiments of the present invention can be practiced generally with any fluid feed stream, including a vapor feed stream. In addition, the method and apparatus disclosed herein can generally be applied or adapted to produce other purified liquid materials, such as ammonia, nitrous oxide, or fluorocarbons, etc. High purity nitrous oxide, ammonia and fluorocarbons also have potential applications in semiconductor fabrication. It is further understood that embodiments of the invention may be practiced with different combinations of one or more features disclosed herein. Thus, although one aspect of the invention provides a purification vessel with an internal storage chamber, an external storage chamber may also be advantageously used in conjunction with other features of the invention.

I claim:

1. A method for producing a purified liquid stream comprising:
   providing a feed stream source;
   introducing under pressure a feed stream from the source to a purification vessel;
   supplying heat to the feed stream by heat exchange with a compressed refrigerant vapor stream in a first heat exchanger;
   distilling the feed stream to form a purified vapor;
   condensing the purified vapor to form purified liquid by heat exchange with a refrigerant liquid stream in a second heat exchanger, wherein the refrigerant liquid stream and the compressed refrigerant vapor stream are provided in a refrigerant flow network comprising the first and second heat exchangers; and
   withdrawing the purified liquid stream from the purification vessel, wherein the feed stream is a liquid carbon dioxide stream, and at least a portion of the heat supplied to the liquid carbon dioxide feed stream at the first heat exchanger is generated from the condensation of the purified carbon dioxide vapor at the second heat exchanger.

2. A method for producing a purified liquid stream comprising:
   providing a liquid material source;
   introducing under pressure a liquid feed stream from the liquid material source to a purification vessel via a substantially free flow connection, the purification vessel comprising a distillation column assembly and a collection chamber positioned annularly about the distillation column assembly;
   purifying the liquid feed stream in the distillation column assembly to produce a purified liquid; and
   storing the purified liquid in the collection chamber.

3. The method of claim 2, wherein the liquid material is selected from the group consisting of carbon dioxide, nitrous oxide, ammonia and fluorocarbons.

4. The method of claim 3, further comprising the step of directing a recycle vapor of the material having impurities via a line to the distillation column assembly in the purification vessel.

5. The method of claim 2, further comprising the step of directing the liquid from the bottom of the purification vessel through a line into the liquid material source.

6. The method of claim 2, further comprising the step of withdrawing the purified liquid stream from the collection chamber of the purification vessel.

7. A method for producing a purified liquid stream comprising:
   providing a liquid material source wherein the liquid material is selected from the group consisting of carbon dioxide, nitrous oxide, ammonia and fluorocarbons;
   introducing under pressure a liquid feed stream from the liquid material source to a purification vessel via a substantially free flow connection, the purification vessel comprising a distillation column assembly and a collection chamber positioned annularly about the distillation column assembly;
   vaporizing the liquid feed stream into a vapor;
   directing the vapor through a distillation column in the distillation column assembly to purify the vapor;
   condensing the purified vapor into a purified liquid;
   collecting the purified liquid in the collection chamber to a predetermined volume; and
   returning a portion of the purified liquid from the bottom of the collection chamber to the distillation column assembly when the predetermined volume has been exceeded.

8. A method for producing a purified liquid stream comprising:
   providing a liquid material source wherein the liquid material is selected from the group consisting of carbon dioxide, nitrous oxide, ammonia and fluorocarbons;
   introducing under pressure a liquid feed stream from the liquid material source to a purification vessel via a substantially free flow connection, the purification vessel comprising a distillation column assembly and a collection chamber positioned annularly about the distillation column assembly;
   vaporizing the liquid feed stream to produce a vapor;
   directing the vapor through a distillation column of the distillation column assembly to produce a purified vapor;
   providing a condenser refrigeration system comprising at least one condenser inside the distillation column assembly;
   condensing the purified vapor into a purified liquid in the at least one condenser;
   collecting the purified liquid in the collection chamber to a predetermined volume;
   withdrawing an amount of the purified liquid from the collection chamber and subjecting the purified liquid to a pressure of from about 1100 to about 3000psia; and
   directing heat byproduct from the condenser refrigeration system to a heat exchanger for heating the purified liquid to a predetermined delivery or storage temperature; wherein the heat byproduct is generated in part by the condensation of the purified vapor in the at least one condenser.

9. An apparatus for producing a purified liquid stream comprising:
   a purification vessel in connection with a bulk material source, the vessel comprising an intake for admitting a bulk material feed stream from the source, a distillation assembly comprising a distillation column for forming a purified vapor from the bulk material feed stream and a condenser for condensing the purified vapor into a purified liquid, and an annular collection chamber surrounding the distillation column for collecting the purified liquid; and
   a refrigerant flow network in communication with the bulk material feed stream and the purified vapor for providing heat to the bulk material feed stream and cooling to condense the purified vapor into the liquid after the purified vapor exits the distillation column.

10. The apparatus of claim 9, wherein the bulk material is selected from the group consisting of carbon dioxide, nitrous oxide, ammonia and fluorocarbons.

11. The apparatus of claim 9, wherein the intake of the vessel is a substantially free flow intake and the bulk material feed stream is a liquid stream.

12. The apparatus of claim 11, further comprising means for transferring a portion of the purified liquid from the annular collection chamber to the distillation column for reflux.

13. The apparatus of claim 11, further comprising means for transferring a portion of the purified liquid formed from the condenser to the annular collection chamber and another portion of the purified liquid to the top of the distillation column.

14. The apparatus of claim 11, wherein a heat byproduct is produced from the refrigerant flow network, the heat byproduct directed to warm the purified liquid.

15. The apparatus of claim 11, wherein the annular collection chamber is an integral 30 component of the purification vessel.

16. The apparatus of claim 11, wherein the annular collection chamber is a discrete component of the purification vessel.

17. The apparatus of claim 11, further comprising a recycle feed line for directing a vapor of the material containing impurities from a point-of-use application to the distillation assembly.

18. The apparatus of claim 11, further comprising a recycle feed line for directing a recycle vapor stream of the material containing impurities from a purification treatment to the distillation assembly.

19. The apparatus of claim 18, wherein the recycle vapor stream from the recycle feed line commingles in the purification vessel with the bulk liquid material.

20. The apparatus of claim 19, wherein the commingled recycle stream and bulk liquid material returns to the bulk material source via the substantially free flow connection.

21. A purification vessel comprising:
a distillation column assembly having an inlet for admitting art amount of material to be purified and an outlet for releasing an amount of purified material, a heat exchanger in contact with the material to be purified, a packed distillation column having a column inlet and column outlet through which material to be purified passes, said exchanger positioned below the column inlet, and a condenser located proximate to the column outlet; and an annular chamber surrounding the packed distillation column, the annular chamber having an inlet for collecting purified material and are outlet for releasing the collected purified material.

22. The purification vessel of claim 21, wherein the material to be purified is a bulk liquid selected from carbon dioxide, nitrous oxide, ammonia and fluorocarbons.

23. The purification vessel of claim 21, wherein the annular collection chamber is integral with the purification vessel.

24. The purification vessel of claim 21, wherein the annular chamber further acts as a storage chamber for the purified material.

25. The purification vessel of claim 21, wherein the annular chamber is a discrete component in the purification vessel.

26. The purification vessel of claim 21, wherein the annular chamber comprises a common outer wall with the purification vessel.

27. An annular chamber for collecting purified liquid carbon dioxide from a distillation column comprising:
a substantially cylindrical vertical inner wall, a chamber bottom extending radially outward from the inner wall a predetermined distance to a substantially cylindrical vertical outer wall, the inner wall having a diameter dimensioned to surround a packed distillation column.

28. The annular chamber of claim 27, wherein the annular chamber further acts as a storage chamber for the purified liquid carbon dioxide.

29. The annular chamber of claim 27, wherein the chamber is an open top vessel.

30. The annular chamber of claim 27, wherein the chamber is a discrete component in a purification vessel containing the distillation column.

* * * * *

UNITED STATES PATENT AND TRADEMARK OFFICE
CERTIFICATE OF CORRECTION

PATENT NO. : 6,912,872 B2  Page 1 of 1
DATED : July 5, 2005
INVENTOR(S) : Walter H. Whitlock It is certified that error appears in the above-identified patent and that said Letters Patent is hereby corrected as shown below:

Column 14,
Line 35, after "column" add, -- , and means for transferring purified liquid carbon dioxide from the distillation column to the annular chamber --.

Signed and Sealed this

Twentieth Day of December, 2005

JON W. DUDAS
*Director of the United States Patent and Trademark Office*